United States Patent [19]

Wong et al.

[11] Patent Number: 5,134,879
[45] Date of Patent: Aug. 4, 1992

[54] TEST METHOD AND APPARATUS

[75] Inventors: Charles F. Wong, Yorba Linda; Rick J. Orth, Diamond Bar, both of Calif.

[73] Assignee: Union Oil Company of California, Los Angeles, Calif.

[21] Appl. No.: 576,361

[22] Filed: Aug. 31, 1990

[51] Int. Cl.$^5$ ............................ G01N 7/10; G01N 3/00
[52] U.S. Cl. .............................. 73/61.72; 73/863.51; 73/863.85
[58] Field of Search ............... 73/61.2, 61 R, 61.4, 73/863.82, 863.85, 863.86, 863.23, 863.11, 863.81, 866.5, 863.51

[56] References Cited

U.S. PATENT DOCUMENTS

| | | | |
|---|---|---|---|
| 2,484,279 | 10/1949 | Folz | 73/86 |
| 4,015,475 | 4/1977 | Pluschkell et al. | 73/866.5 |
| 4,309,899 | 1/1982 | Torres | 73/86 |
| 4,481,833 | 11/1984 | Bajek | 73/863.23 |
| 4,653,334 | 3/1987 | Capone | 73/863.81 |
| 4,697,465 | 10/1987 | Evans et al. | 73/866.5 |
| 4,978,506 | 12/1990 | Calderwood | 73/863.23 |

OTHER PUBLICATIONS

"Standard Practices for Sampling Water-Formed Deposits", pp. 556-562 ASTM Designation D887, by American Society for Testing and Materials, Approved 1982.

"Field Evaluation of Sampling Methods for Pressurized Geothermal Liquids, Gases, and Suspended Solids", Jan. 1980, Pacific Northwest Laboratory, Battelle Memorial Institute, Report #PNL-3412/UC-GEd, Chapter 9, pp. 9.1-9.23 and Appendix A.

Primary Examiner—Hezron E. Williams
Assistant Examiner—Michael J. Brock
Attorney, Agent, or Firm—Gregory F. Wirzbicki; William O. Jacobson

[57] ABSTRACT

In-stream suspended solids measurement in geothermal brine is accomplished by removal of suspended solids under process conditions followed by cooling using a detachable probe assembly. The cooling inhibits precipitation of added solids. By placing an in-stream filter at the sample entrance to immediately collect and remove suspended solids, pressure drop across the filter can be used to obtain real time suspended solids measurements. The filter may be composed of non-reactive/non-scaling materials and exposed for short durations to avoid additional chemical reaction and precipitation/scale at the filter. The detachable probe is attached to a valved access to the process stream allowing detachment and device weighing (instead of scale removal and weighing) to also provide suspended solids measurements. The assembly includes an extension pipe to contain the process stream pressures, a mounting for a Pitot tube or coupon on a translatable shaft or tube which can be translated through the valved access to the process stream, and a vent valve to seal and control pressure in the extension pipe. A fluid collection system includes a cooling surface and collection vessel.

27 Claims, 1 Drawing Sheet

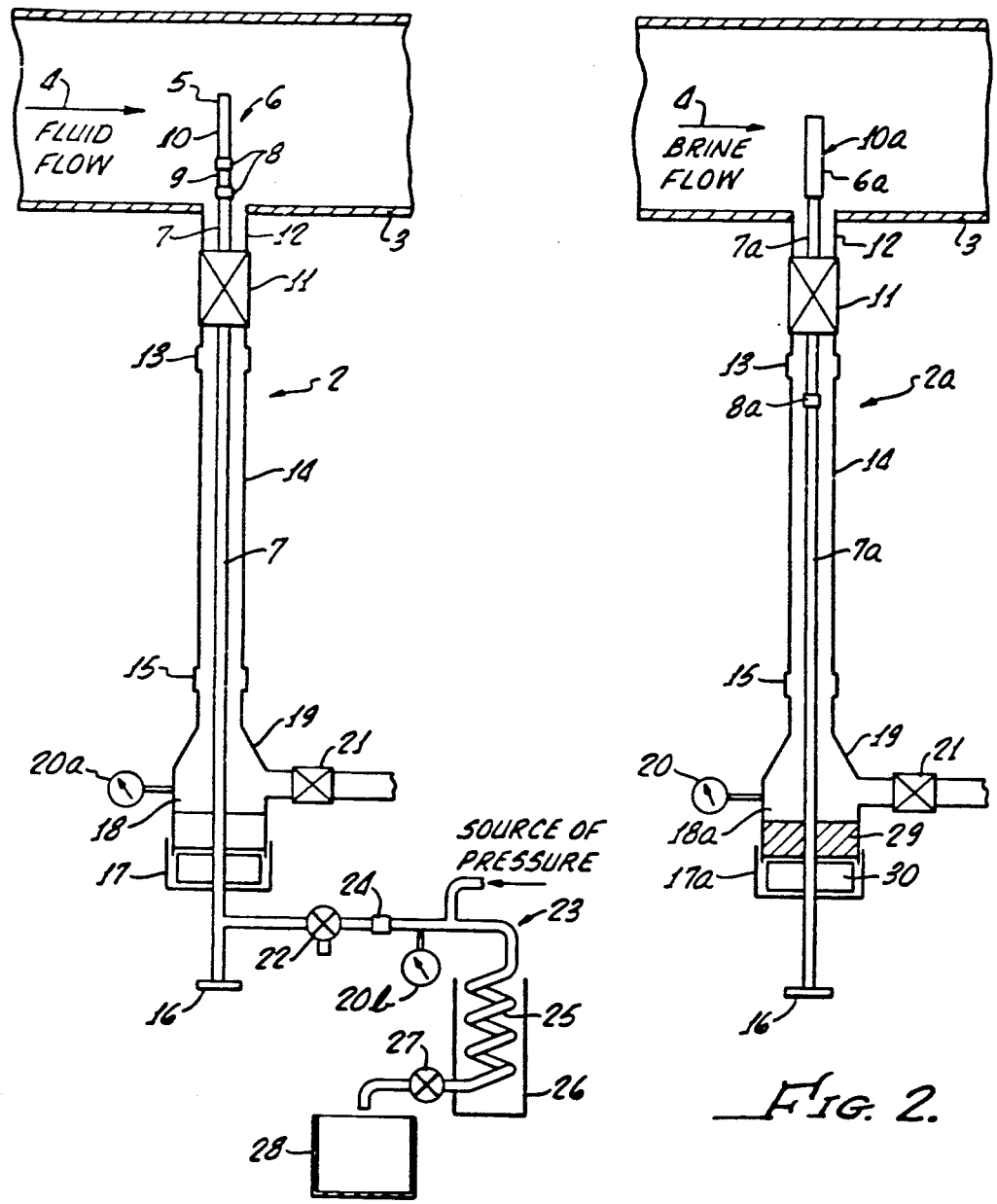

TEST METHOD AND APPARATUS

FIELD OF THE INVENTION

This invention relates to devices and methods to measure entrained and deposited solids in a fluid process system. More specifically, the invention provides an accurate suspended solids test for geothermal brine systems.

BACKGROUND OF THE INVENTION

Many industrial processes must handle fluids which also include solids in the form of entrained particles or precipitate (i.e., suspended solids). Due to temperature, pressure and other operating condition changes, these solids can deposit on the walls of the fluid process system in the form of scale, causing fluid handling problems and plug subsurface geothermal formations and injection wells. This can require special handling equipment (e.g., filtration) and special procedures, such as periodic back-flush or shutdown for solids removal and rework of injection wells. These added solids handling facilities and procedures can consume significant time, energy, and expense. In addition, facilities and procedures which are cost effective for one type and amount of solids may be ineffective for other types and amounts of solids, e.g., chemical cleaning can be quick and effective for removing a small amount of calcium carbonate-rich scale, but very costly (or even ineffective) for smaller amounts of carbonate in heavier scale deposits.

The ability to accurately forecast and/or measure solids in a fluid handling system (without shutting down the process) would minimize these handling problems and costs. Accurate forecast and measurements would allow optimization of solids removal efforts.

However, fluid process conditions (e.g., elevated temperature and pressure) can cause measurement problems. Limited fluid system access during production or other activities may also be a problem. These measurement problems have typically required sampling, rather than direct in-stream measurement. A typical sampling device is a Pitot tube which diverts a fluid (and suspended solids) to an ambient temperature and pressure collection device. The collected sample is then later analyzed in a laboratory.

In some process industries, such as geothermal energy extraction, these measurement difficulties are greatly compounded. The process fluid (brine) is saturated or supersaturated with scale-forming dissolved solids and acid gases. Usually, energy is extracted from geothermal brine by flashing to produce steam, which is then used to drive a steam drive. The flashing procedure, however, also lowers the pressure and temperature of the remaining geothermal brine which in turn tends to reduce solubility and supersaturate the dissolved solids and liberate gases. The supersaturated solids, liquids, and remaining gases may rapidly undergo chemical changes so that standard sampling and testing techniques generate erroneous results. For example, suspended solids measurement may erroneously include post-sampling precipitation. Still further, the scaling and rapid precipitation can clog or otherwise adversely affect sampling devices and methods.

A fluid sampling device has been developed by Battelle Memorial Institute for the U.S. Department of Energy at Pacific Northwest Laboratory. As disclosed in Technical Report No. PNL3412, UC66d, dated January 1980, Chapter 9 by R. P. Smith, the Battelle suspended solids sampling device is designed specifically for geothermal fluids. The device obtains a fluid and suspended solids sample in a Pitot tube-like probe and conduit. The sample conduit diverts the fluid sample out of the process flow stream to a heat exchanger to quickly cool the fluid (tending to stabilize the mixture by reducing the rapid rate of chemical reaction and precipitation). After cooling, the device filters the sample to remove the suspended solids. Any remaining liquid sample is then collected for laboratory analysis.

Although the rapid precipitation rate is reduced and suspended solids are removed by the Battelle sampling device, measurement problems remain. Diverting the suspended solids in the sample line may deposit suspended solids before collection and accelerate precipitation reactions. Sample cooling slows but does not stop precipitation. Sample cooling thermal gradients may also cause further deposition of the sampled suspended solids before filtration. Thus, even if the fluid (and entrained suspended solids) sample is initially representative, the sample quickly becomes unrepresentative.

Another measurement approach is to provide a process fluid side stream. The side stream is periodically isolated (without disturbing the main process system) and fluid samples or coupons removed for measurements. Coupons or other surfaces in the side stream are exposed to flowing brine to represent main process system surfaces under process conditions. After exposure to the coupons, the side stream fluids may be returned to the main stream or separately discharged.

However, side stream measurements have also been inaccurate. Side stream fluid conditions cannot fully duplicate main stream conditions. Diversion to the side stream may again cause unrepresentative scaling/precipitation. Although brine is flowing, side stream geometry is different (e.g., smaller side stream geometry can provide more pipe contact area for precipitation than main process stream). Flow distribution conditions are also different from the process stream. These differences can affect precipitation, scale formation and solids measurement.

Besides these problems, the suspended solids measurement device and method must also be able to handle a variety of process conditions. A sampled or side stream measurement may be nearly representative at certain fluid process conditions, but not at others, such as part load operation. The measurement device should also be capable of providing rapid measurements in response to changes in process conditions.

None of the current approaches known to the inventors eliminate the aforementioned side stream and sample collection problems. In addition, the problem of periodic solids removal from side stream or sampling apparatus remains.

SUMMARY OF THE INVENTION

Such problems are avoided in the present invention by providing a concurrent in-stream suspended solids measurement and liquids collection device. The device uses a first replaceable probe in a removable sampling device. Like the common Pitot tube, the present invention obtains a representative sample of fluid, but an in-stream filter at the sample entrance port immediately collects and removes suspended solids before significant additional precipitation or other chemical changes occur. The remaining liquid is quickly cooled under pressure and collected in non-scaling equipment. A real time indication of suspended solids is obtainable from a pressure drop measurement across the filter, in addition to removal and direct measurement of filtered solids.

The first probe can be replaced with a second probe inserted into the process stream. The second probe exposes a solids collection surface to collect scale. A real time estimate of scale can be obtained by drag force or pressure drop measurement, as well as direct measurement of the scaled probe. The in-stream sampling, redundant real time data, and initial separation of suspended solids result in accurate solids and other fluid measurements. The replaceable probe device also allows complementary fluid measurements further assuring accuracy.

The replaceable feature is achieved by mounting the probes to a movable shaft within an extension pressure containment pipe attached to a valved access to the process stream. The shaft is hollow to conduct the collected liquid sample to a collection vessel. The shaft moves from a sampling position (through opened access valve) to a withdrawn position (allowing access valve to be closed).

The process of using the removable assembly attaches the pipe to the valved process access port. The access valve is opened and the shaft translates the sample probe into the fluid process stream. After measurement and/or sample collection, the probe is withdrawn and access valve is closed. After venting, the probe can be removed and replaced with a different insertable probe. Corrosion probe can also be installed to measure the corrosion rate of the fluid handling system.

The present invention is expected to be accurate under off-design conditions because of the immediate separation of suspended solids, quick cooling under pressure to inhibit further precipitation (maintaining fluid chemistry), and multiple sample probe capability. The multiple probe ability provides redundancy and alternative property measurement capability.

The present apparatus and method achieves (1) accurate measurement of in-stream suspended solids, (2) accurate measurement of in-stream scaling rate, and (3) accurate measurement of in-stream corrosion rate. The in-stream measurements avoid errors caused by sample withdrawal or side stream diversions which change the condition of fluid and measured fluid and handling system properties.

BRIEF DESCRIPTION OF THE DRAWINGS

FIG. 1 shows a schematic side view of a sampling apparatus having a solids filtering measurement probe; and FIG. 2 shows a cross-sectional schematic view of a sampling assembly similar to that shown in FIG. 1 having a solids measurement probe for scaling or corrosion.

In these Figures, it is to be understood that like reference numerals refer to like elements or features.

DETAILED DESCRIPTION OF THE INVENTION

FIG. 1 shows a schematic cross-sectional view of a solids filtering measurement apparatus 2 attached to a portion of a fluid handling system or process pipe 3. The pipe 3, handles a flow of elevated temperature fluid mixture or brine 4 (shown as an upstream fluid flow direction arrow within pipe 3) which includes suspended solids. In geothermal steam gathering or flash systems, the brine is also supersaturated in dissolved solids, such as silica and sulfide. The suspended solids and supersaturation at elevated temperatures generate ongoing precipitation of silica particulates and scale of the inside (fluid contacting) surfaces of the pipe 3. An opening 5 in a measuring device or sampling probe 6 opens to the upstream direction in order to obtain a fluid 4 sample within the probe 6. The sampling probe 6 portion of the solids measurement apparatus 2 is a tubular member attached at a sample probe mounting surface on hollow shaft 7 by union 8 (each of two union parts shown exploded for clarity) which diverts a fluid (and entrained suspended solids) sample out of the pipe 3. Proximate to the opening 5 is a filter or screen 9 for separating suspended solids which is held in place between the probe 6 and the mounting surface on hollow shaft 7 by the union 8. The sampling probe 6 may also include a scale testing material surface 10. Although the test material surface 10 is shown on the upstream facing surface, downstream or other surface or protrusions of the probe 6 in the stream flow may be used.

Alternative embodiments may place the filter 9 closer to the opening 5 or even in-line with the flow direction 4 (e.g., rotated 90 degrees and placed at the opening 5). However, since the probe assembly 6 must be insertable and withdrawable on shaft 7 through an access valve 11 when opened, valve limited in-line dimensions and placement may require placement of the filter 9 as shown.

The process stream access valve 11 is attached on one side to a process pipe tee or other process port 12 and a means for sealing and unsealing the port 12. Access valve 11 is preferably a gate or other full opening type of shutoff valve. A first coupling 13 attaches a fluid containment conduit or extension pipe 14 to the other side of access valve 11. The extension pipe 14 provides a length to withdraw shaft 7 and attached sample probe from the process stream 4 while containing the pressurized brine 4 when access valve 11 is open. Shaft 7 is within tee 12, open access valve 11 and extension pipe 14 when shaft 7 is in the sampling position as shown.

The protruding handle 16 attached to shaft 7 and the length of extension pipe 14 (from first coupling 13 to second coupling 15) allow the probe assembly 6 to be withdrawn into the extension pipe 14 when the shaft 7 is moved downwardly and out of the process pipe 3 to the withdrawn position (not shown). Movement (in a transverse direction) is accomplished by pulling (radially outward from fluid flow direction 4) or screwing on handle 16. The shaft 7 is slidably sealed by sheath or packing gland 17 near the handle 16. The sheath 17 is attached to a pressure control box 19 which is attached to the extension pipe 14 by the second coupling 15. Pressure in the annulus 18 between the walls of the box 19 and the shaft 7 is measured by one of two pressure gauges 20a. Fluid pressure in the box 19 can be vented through vent valve 21. If a pressurized fluid supply (not shown for clarity, but similar a source of pressure arrow shown leading to collection tubing 23) is attached downstream of the vent valve 21, the annulus 18 can be pressurized with inert gas such as nitrogen before opening access valve 11 when vent valve 21 is opened.

A first sample valve 22 is a control for the fluid sample pressure and flow through the sampling probe 6 and hollow shaft 7. The first sample valve 22 is attached to collection tubing 23 by union 24. The collection tubing 23 is preferably flexible to allow transverse motion of the shaft 7. Alternatively, rigid collection tubing 23 may be attached when the shaft is in one position and removed by disconnecting union 24 prior to changing the position of shaft 7. The collection tubing 23 includes a heat exchanger portion 25. As shown, this tubing portion 25 may be helical portion of collection tubing within a cooling vessel 26. The cooling vessel 26 may be filled with an ice bath (not shown) to cool the fluid sample within collection tubing 25. Other types of fluid heat exchangers may also be used.

A second sample valve 27 is a second control of the flow and pressure within the collection tubing 23. Second sample valve 27 is located downstream of the first sampling valve 22 proximate to a collection vessel 28. Pressure can be measured by a second pressure gauge 20b attached to the collection tubing 23. Although shown schematically as open vessels, the cooling and collection vessels 26 and 28 may be closed (pressurizable) fluid containers. The collection vessel 28 may be transported to a laboratory for measurement and analysis of the fluid sample.

FIG. 2 shows a cross-sectional schematic view of a similar sampling assembly 2a having replaced the fluid probe and hollow shaft. The brine flow direction 4 is again shown as an arrow within a fluid process handling system or pipe portion 3. The solids sampling probe 6a portion of the measurement apparatus 2a is either a solids collection or corrosion probe coupon attached at a sample probe mounting surface on solid shaft or arm 7a at joint 8a. The sampling probe 6a holds a solid or screen-like scale testing material surface 10a.

The first or process stream access valve 11 is attached on one side to a process pipe tee or other process port 12 and is preferably a gate or other full opening type of shutoff valve. A first coupling 13 attaches an extension pipe 14 to the other side of access valve 11. Solid shaft 7a is within tee 12, open access valve 11 and extension pipe 14 when shaft 7a is in the sampling position (as shown). The extension pipe 14 again provides a pressure containment for the brine 4 when access valve 11 is open.

The length of extension pipe 14 (from first coupling 13 to second coupling 15) allows the probe assembly 6a to be withdrawn into the extension pipe 14 when the solid shaft 7a is moved down and out of the process pipe 3. Movement (in a transverse direction) is again accomplished by manually pulling outward on handle 16. The handle 16 is attached to a protruding end of shaft 7a.

The shaft 7a is slidably sealed by sheath or packing gland 17a near the handle 16. The sheath 17a is adjustably (e.g., threadably) attached to the box 19. Packing material 29 is one means for allowing the shaft 7a to move transversely while containing the brine and may be composed of Teflon. Although heavy scaling is not expected at the end of the shaft near the packing, the shaft sliding contact with the packing is also a means of removing soft or loose scale on the shaft 7a (i.e., motion of shaft against packing tends to scrape off scale deposits on shaft 7a). Tightening (e.g., screwing) the sheath compresses the packing to seal the shaft 7a (preventing brine from leaking outside box 19) and also tends to removably secure the shaft 7a in place if sufficiently compressed. Other means for removably securing the shaft, such as a set screw, can also be used. An alternative means of sealing while allowing transverse motion is a piston in cavity 30.

Pressure in the annulus 18a between the walls of the box 19 and the shaft 7a is measured by pressure gauge 20. Fluid pressure in the box 19 can be vented through vent valve 21. If a pressurized fluid supply (not shown for clarity) is attached to the vent valve 21, the annulus 18a can also be pressurized prior to opening access valve 11.

The process of using the sampling apparatus (having either of the probes and shafts shown in FIGS. 1 and 2) is to assemble the apparatus (when access valve is closed) to access valve 11 with either the fluid sampling probe 6 or solid probe 6a attached to the shaft 7 or 7a. Solid probe 6a may also be attached to the hollow shaft 7 at the mounting surface if the sampling valve 22 or other sealing means is provided. Apparatus may also be pre-assembled. Second valve 21 is closed to form a fluid container.

To prevent oxidation of brine 4 and an unrepresentative surge of brine 4 into the sample conduit (hollow portion of the probe and shaft plus collection tubing) when the access valve 11 is opened, the sample conduit is first purged (valves 21 and 27 open) with and then pressurized (valve 21 and 27 closed through first sample valve 22 using an inert fluid pressure source, such as nitrogen (shown schematically as source of pressure arrow in FIG. 1). The annulus 18a may also be separately pressurized to a pressure comparable to the process stream through vent valve 21 before opening access valve 11 to the process stream if a pressure source (not shown) is attached downstream of vent valve 21. Heat exchanger 25 and vessel 26 may also be used to condition or change the temperature of the inert gas in the annulus 18 to avoid a thermal gradient.

The inert gas pressurization prevents exposure to air (oxidation) and flashing of the brine and also allows leakage testing to be accomplished. External (e.g., at couplings) and internal leakage (e.g., through vent valve 21) can be checked using a variety of known leak test means. Source of inert gas pressure is disconnected or otherwise isolated from the sampling apparatus when the apparatus is leak tested and pressurized.

When annulus and sample conduit inert gas pressure is comparable to the process stream and the source is isolated, first sample valve 22 and/or vent valve 21 is closed and access valve 11 is fully opened. Additional leak testing may also be accomplished at this point, if required. Handle 16 is used to push the shaft 7 or 7a and attached probe 6 or 6a into the process stream 4 through open access valve 11 and the shaft position secured by tightening sheath 17.

Suspended solids measurement may be desired when the brine feed stream 4 is flowing at various velocity distribution conditions. The transverse movement of shaft 7 allows placement of opening 5 at various locations across the pipe 3 diameter or at a single representative location. A preferred representative location of the opening 5 is at the center of the pipe 3. Similarly, a representative or traverse of locations of the solid probe 6a can be selected.

If a fluid sample is to be obtained using probe 6, first and second sample valves 22 and 27 are opened. Opening of these valves can be set to minimize the disturbance of the velocity profile within pipe 3. Sample velocity across opening 5 can approximate velocity prior to sample probe insertion, minimizing disturbance to velocity conditions in pipe 3. Hot process fluid flows through opening 5 and filter 9 prior to being cooled in heat exchanger portion 25 and discharged into collection vessel 28. When a sufficient fluid sample quantity is collected in collection vessel 28, one of the sample valves may be closed and collection vessel isolated.

During the fluid collection, the difference in pressure between the process stream pressure in pipe 3 and sample fluid pressure (e.g., as measured by the pressure gauge 20b attached to the collection tubing 23) can be used to determine the quantity of suspended solids collected by filter 9. An initial or baseline pressure difference, if any, is primarily a function of sample conduit pressure losses (e.g., shaft 6 pressure losses). Any further increase in pressure difference should primarily be caused by filter 9 accumulation of suspended solids (i.e., pressure loss across the loaded filter).

After exposure of coupon or test surfaces 10 or 10a and/or fluid sampling is completed, shaft 7 or 7a is unsecured and attached probe 6 or 6a is withdrawn from the process stream through access valve 11 and the access valve closed. Pressurized fluid brine within the annulus 18 or 18a and the sample conduit can be vented through vent valve 21 and purged with nitrogen using the inert gas supply, if present. First coupling 13 may then be safely disassembled and the probe removed. Removal of scale or other deposits may also be accomplished, if required. The probe may be replaced with a different type and material of construction and inserted as above.

The replaceable probe or corrosion coupon feature allows different samples to be collected or corrosion rate to be measured at the same point in the process stream. Different sample probes can be used to provide redundant measurements or to complement prior measurements. The removable feature also allows direct weighing of components (difference before and after exposure measures the weight of collected scale and suspended solids) without scraping and separate weighing.

In operation, the invention is expected to be used for short and long term exposures in the process stream. Fluid samples (and associated suspended solids measurements) can generally be obtained in less than one hour, preferably in less than 5 minutes. In contrast, scaling probes or corrosion coupons may be left exposed for days or months prior to withdrawal and direct measurement. Real time data and withdrawal decisions may also be based upon pressure loss across the sampling probe (i.e., pressure difference between upstream and downstream of probe locations within the process pipe 3), indicating scale quantity.

The invention satisfies the need to obtain real time and in-process stream measurements. Initial removal of suspended solids at nearly in-stream conditions, pressure difference measurements, repeatability, probe replacement ability and quick sampling avoid delayed, unrepresentative, and unreliable measurement problems of prior devices.

The invention allows accurate sampling during startup, shutdown, steady state, and upset process conditions. Further advantages of the invention include: safety (leak testing and venting before direct access), reliability (redundant and complementary measurements), and maintenance (removal and disassembly allows easy cleaning).

Although the maximum and minimum temperature and pressure of the brine process stream are theoretically unlimited, the brine temperature is typically limited to a range of from near ambient to 320° C. preferably from about 100° C. to about 250° C. The geothermal brine pressure is typically within a range of about one atmosphere to 40 atmospheres, preferably from about one atmosphere to about 30 atmospheres.

The size of the sampling apparatus is also similarly theoretically unlimited. However, the access valve that is preferred is a 2.54 cm (1 inch) nominal full flow valve. Probe assemblies and shafts must have dimensions which allow passage through this size access valve.

Alternative embodiments allow different probes, such as corrosion coupons to be directly exposed and removed from the process stream. Other replaceable probes can be designed to measure fluid velocity, flow rate, density, or other fluid properties within the process stream. Still other probes could be designed to measure the properties of the filtered solids within the process stream, such as fiber optics or other detector means.

Still other alternative embodiments are possible. These include: a scraper mounted on the shaft 7 or 7a to better remove accumulated scale in the annulus when the shaft is moved; a plurality of openings (e.g., an annular type of device) in a fluid sample probe instead of the single fluid opening 5; an expandable or bendable probe which could sample at any point within the process pipe 3 and could be bendably or compressively withdrawn through the access valve; a series of openings 5 at different radial and axial positions along the shaft/probe so that shaft rotation would expose a series of openings to the flow direction 4 without replacement; a remotely operated valve at opening 5; a plurality of shafts and probes insertable upon access valve opening; adding a flexible washer to the shaft proximate to the wall 3 when in the sampling position to simulate the wall of the pipe 3; providing a mechanized means for moving the handle 16 and shaft 7 or 7a; having the fluid sample conduit (i.e., probe, shaft and collection tubing) be composed of or coated with non-scaling or scale resistant materials, such as Teflon reinforced materials; having components (e.g., extension pipe 14) be composed of transparent materials to observe position and scale buildup; connecting the collection tubing directly to an analysis instrument instead of a collection vessel 28 for later analysis; and insulating the external apparatus surfaces to reduce thermal gradients and losses.

While the preferred embodiment of the invention has been shown and described, and some alternative embodiments also shown and/or described, changes and modifications may be made thereto without departing from the invention. Accordingly, it is intended to embrace within the invention all such changes, modifications and alternative embodiments as fall within the spirit and scope of the appended claims.

What is claimed is:

1. An in-situ measurement apparatus for measuring suspended solids present in a fluid contained within a fluid handling system comprising:
   a fluid handling system port;
   a valve attached to said system port and capable of sealing and unsealing said system port and forming a sealable port;
   a pipe attached to said sealable port;
   a translatable arm at least partially containable within said pipe and capable of being translated from a sampling position to a withdrawn position;
   at least one compositional fluid property measuring device at least one portion of which is removably attachable to said arm, said one portion having a sample port for obtaining a sample of said fluid, a filter, and a conduit for obtaining a fluid sample and directing said sample through said sealable port when said one portion is attached to said arm in said sampling position and said sealable port is unsealed, said one portion being positioned clear of the interior of said valve when said arm is in said withdrawn position; and wherein said filter is capable of separating at least a portion of said suspended solids from said sample when said filter is generally located within said fluid system and at or near said sample port.

2. A measurement apparatus for measuring suspended solids present in a fluid contained within a fluid handling system comprising:

a fluid handling system port;

means for sealing and unsealing said port;

a fluid containment device attached to said fluid system port;

a translatable arm at least partially containable within said fluid containment device and capable of being translated from a sampling position to a withdrawn position;

at least one compositional fluid property measuring device at least one portion of which is removably attachable to said arm, said one portion having a sample port for obtaining a sample of said fluid, means for separating an amount of said suspended solids from said sample, and means for directing said sample through said system port when said one portion is attached to said arm in said sampling position and said port is unsealed, said one portion being positioned clear of said sealing means when said arm is in said withdrawn position; and wherein said means for separating is capable of separating and removing at least a portion of said suspended solids from said sample and said separating means is located generally within said fluid system at or near said sample port.

3. The apparatus of claim 2 which also comprises means for collecting said fluid sample comprising:

a fluid collection container;

a duct connecting said fluid sampling device to said fluid collection container; and means for closing said fluid sample within said duct.

4. The apparatus of claim 3 wherein another of said devices is attachable to a probe mounting surface on said arm and comprises:

a corrosion and scale probe measuring device attachable to said probe mounting surface, wherein said corrosion and scale measuring device is within said fluid system when attached and said arm is in said sampling position, and capable of retraction through said port to within said fluid containment device when said arm is in said withdrawn position; and means for removably attaching said scale sampling device to said mounting surface.

5. The apparatus of claim 4 wherein said means for sealing and unsealing is a full flow shutoff valve.

6. The apparatus of claim 5 wherein said means for separating is a screen.

7. The apparatus of claim 5 wherein said means for separating is a filter.

8. The apparatus of claim 7 wherein said means for directing is a sample conduit within said device.

9. The apparatus of claim 8 wherein said means for cooling is a heat exchange surface.

10. The apparatus of claim 9 wherein said means for removably attaching is a coupling.

11. The apparatus of claim 10 wherein said fluid sampling device has a plurality of sample ports.

12. The apparatus of claim 11 which also comprises a source of inert gas attached to said duct.

13. The apparatus of claim 12 which also comprises a means for removing scale in said fluid containment device when said arm is moved.

14. The apparatus of claim 13 which also comprises a means for securing said arm in a position.

15. A process for measuring suspended solids in a fluid mixture at elevated temperature and pressure conditions within a fluid handling system having a closable access port comprising:

attaching a fluid containment and translatable collector device to said access port when closed;

opening said access port;

inwardly translating at least a portion of said collector device through said open access port to a sampling position wherein said collector is exposed to said fluid mixture within said fluid handling system;

collecting a fluid mixture sample at about said elevated temperature and pressure conditions;

separating said suspended solids from said sample at about said conditions;

cooling said fluid mixture after said separating step;

outwardly translating said collector portion through said open access port to a withdrawn position wherein said collector portion is removed from said access port;

closing said access port; and wherein said collecting step also comprises measuring at least two fluid system pressures at locations upstream and downstream of said collector portion.

16. The process of claim 15 which also comprises calculating the quantity of collected suspended solids based at least in part upon said measured fluid system pressures after said collecting step.

17. The process of claim 16 wherein said outwardly translating step is accomplished after a first quantity of collected suspended solids is calculated based upon a difference in pressures measured at said upstream and downstream locations.

18. The process of claim 17 wherein said fluid is a geothermal brine at a temperature of at least 100° C. and after said closing step also comprises the steps of:

detaching said fluid containment and translatable collector device; and weighing said detached device.

19. The process of claim 18 which also comprises the step of purging said device with an inert gas from an inert gas source prior to said opening step.

20. The process of claim 19 wherein said purging step essentially avoids contact between said fluid mixture sample and oxygen.

21. The process of claim 20 wherein said purging step also comprises leak testing said device.

22. The process of claim 21 which also comprises the step of isolating said device from said source of inert gas after said purging step.

23. The process of claim 22 which also comprises the step of venting said device prior to said detaching step.

24. The process of claim 23 which also comprises the step of releasably securing said portion of said device in said sampling position after said inwardly translating step.

25. The process of claim 24 which also comprises the step of releasing said secured portion of said device before said outwardly translating step.

26. The process of claim 23 wherein said inwardly translating step also comprises selecting said sampling position such that said sample is essentially representative of said fluid.

27. The process of claim 24 which also comprises the step of removing said device and replacing said device with a second device capable of unequal sample collection after said detaching step.

* * * * *

UNITED STATES PATENT AND TRADEMARK OFFICE
CERTIFICATE OF CORRECTION

PATENT NO. : 5,134,879
DATED : August 4, 1992
INVENTOR(S) : Wong, et al

It is certified that error appears in the above-identified patent and that said Letters Patent is hereby corrected as shown below:

ON THE TITLE PAGE:

Cover sheet, the title, delete "TEST METHOD AND APPARATUS" and change to -- METHOD AND APPARATUS FOR IN-STREAM MEASUREMENT OF SUSPENDED SOLIDS IN GEOTHERMAL BRINE --.

Claim 26, column 10, line 61, change "23" to -- 25 --.

Claim 27, column 10, line 64, change "24" to -- 26 --.

Signed and Sealed this

Tenth Day of August, 1993

Attest:

MICHAEL K. KIRK

Attesting Officer   Acting Commissioner of Patents and Trademarks